(12) United States Patent
Balboa et al.

(10) Patent No.: US 11,090,038 B2
(45) Date of Patent: Aug. 17, 2021

(54) SUTURE-LENGTH COMPENSATING ANCHOR SYSTEM AND METHOD

(71) Applicant: Smith & Nephew, Inc., Memphis, TN (US)

(72) Inventors: Marc J. Balboa, Hopkinton, MA (US); Geoffrey I. Karasic, Milton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 280 days.

(21) Appl. No.: 16/191,943

(22) Filed: Nov. 15, 2018

(65) Prior Publication Data

US 2019/0159771 A1     May 30, 2019

Related U.S. Application Data

(60) Provisional application No. 62/590,931, filed on Nov. 27, 2017.

(51) Int. Cl.
| | | |
|---|---|---|
| *A61B 17/04* | (2006.01) | |
| *A61B 17/88* | (2006.01) | |
| *A61B 17/3205* | (2006.01) | |
| *A61B 17/00* | (2006.01) | |
| *A61B 90/00* | (2016.01) | |

(52) U.S. Cl.
CPC ...... *A61B 17/0401* (2013.01); *A61B 17/0485* (2013.01); *A61B 17/8861* (2013.01); *A61B 17/8872* (2013.01); *A61B 17/32056* (2013.01); *A61B 2017/00477* (2013.01); *A61B 2017/044* (2013.01); *A61B 2017/0409* (2013.01); *A61B 2090/034* (2016.02)

(58) Field of Classification Search
CPC ............ A61B 17/0401; A61B 17/0485; A61B 17/864; A61B 17/8861; A61B 17/8872; A61B 2017/0409; A61B 2017/0412; A61B 2017/0414; A61B 2017/0427; A61B 2017/044; A61B 2017/0441; A61B 2017/0445; A61F 2/0811; A61F 2002/0858; A61F 2002/0882; A61F 2002/0888

See application file for complete search history.

(56) References Cited

U.S. PATENT DOCUMENTS

| | | | |
|---|---|---|---|
| 2008/0306511 A1 | 12/2008 | Cooper et al. | |
| 2009/0264924 A1* | 10/2009 | Ushiba | A61B 17/864 606/228 |
| 2011/0319932 A1* | 12/2011 | Avelar | A61B 17/06166 606/228 |
| 2012/0053628 A1* | 3/2012 | Sojka | A61B 17/0485 606/232 |
| 2014/0081324 A1* | 3/2014 | Sengun | A61B 17/0401 606/232 |

\* cited by examiner

*Primary Examiner* — Robert A Lynch
(74) *Attorney, Agent, or Firm* — Norman F. Hainer, Jr.

(57) ABSTRACT

Embodiments of the invention include methods and devices for coupling to a suture with a suture anchor. The suture anchor may include a cavity in which a length of suture may be drawn prior to insertion and from which that length of suture may be drawn out as the suture anchor is implanted. Therefore, in some embodiments, suture may be drawn out of the cavity from the length of suture rather than from working portions of the suture that extend outwardly from the tissue in which the suture anchor is being implanted.

23 Claims, 11 Drawing Sheets

SUTURE-LENGTH COMPENSATING ANCHOR SYSTEM AND METHOD

FIELD OF THE INVENTION

The present invention relates generally to the field of tissue anchors, and more particularly relates to suture anchors and related methods. Some embodiments provide for interaction between a suture and a suture anchor that reduces twisting and pulling on the suture during suture anchor implantation.

BACKGROUND

It is advantageous for a suture anchor not to twist or pull suture into an anchor hole during anchor implantation. This need has been addressed in the prior art by multiple part anchors that are first advanced and then used to clamp onto suture by activation of at least one of the multiple parts of the anchor. A multiple part anchor is, however, categorically more complex and more expensive than a unitary anchor. However, some issues with a typical prior art unitary anchor are: 1) the anchor may twist suture as the anchor is rotated or screwed into the bone; and 2) the anchor may drag or pull suture from tissue connected ends of the suture into the bone hole when the anchor is inserted, which may over-tension tissue connected to the ends.

It would be advantageous to provide suture anchors and insertion instruments configured to draw a length of suture into the suture anchor prior to implantation such that the length of suture may be drawn from the suture anchor during implantation, rather than suture being drawn from free or tissue connected ends of the suture. It may be further advantageous to provide coordination between a suture anchor and an insertion instrument, such as a tissue puller, either by releasing, twisting with, or partial relative release, that reduces twisting and pulling of suture by the anchor relative to the insertion instrument.

SUMMARY

An embodiment of the invention is a suturing system with a suture anchor, an inserter, and a suture puller. The suture anchor may include a body that has an outer surface configured to engage with a bone in which the suture anchor is implantable, and a cannulation through the body. Embodiments of the inserter have a proximal end configured to be manipulated by a user, and a distal end configured to releasably engage with the suture anchor. Embodiments of the suture puller are configured to be proximally and distally movable relative to the inserter and may include a shaft with a proximal end and a distal end, and a suture retainer near the distal end of the shaft. The suture retainer may also be configured and sized to fit into the cannulation through the body to couple to a portion of a suture near a distal end of the suture anchor and be used to pull the portion of the suture proximally into the suture anchor.

Another embodiment of the invention is a method of concurrently implanting a suture and a suture anchor into a bone. The method embodiments may include drawing a length of suture into a cavity in the suture anchor, and moving the suture anchor distally into the bone to implant the suture anchor into the bone while allowing the length of suture drawn into the suture anchor to be drawn out of the suture anchor distally proportional to the amount the suture anchor is moved distally into the bone.

Still another embodiment of the invention is a method of securing a suture to a bone that includes at least placing an inserter within a tube, placing a suture anchor at a distal end of the tube, wherein the suture anchor is configured to couple with the inserter, and placing a suture puller with a suture retainer near its distal end within the inserter and within the suture anchor. The method may further include positioning the suture puller distally relative to the inserter and the suture anchor so that the suture retainer is accessible from a distal end of the suture anchor and coupling a length of suture with the suture retainer. The suture puller may then be moved proximally relative to the suture anchor to draw the length of suture into a cavity in the suture anchor, and the tube and the suture anchor may be moved distally into the bone to implant the suture anchor into the bone while allowing the length of suture drawn into the suture anchor to be drawn out of the suture anchor distally proportional to the amount the tube and the suture anchor are moved distally into the bone. Embodiments of the method may also include releasing the suture from the suture retainer.

DETAILED DESCRIPTION

A suturing system 1 with a suture anchor 100, an inserter 200, a suture puller 300, and a suture 400 is shown in whole and in respective part in FIGS. 1-7. The suture anchor 100, as shown in more detail in FIGS. 2 and 7, may include a body 110 that has an outer surface 120 configured to engage with a bone 5 in which the suture anchor 100 is implantable, and a cannulation 115 through the body 110. The suture anchor 100 is similar to a HEALICOIL™ brand suture anchor offered by Smith and Nephew, Inc., but includes an open distal end through which the suture puller 300 may be used. The illustrated suture anchor 100 is a unitary suture anchor having no components that are adjustable relative to one another. It is known in the prior art to manage suture tension by providing suture anchors that have parts that move relative to one another and clamp or pinch suture between the parts upon activation. This, however, requires greater manufacturing expense and complexity. Some embodiments of the present invention may include more than one part, but where the multiple parts do not affect a unitary type effective function of the device, the suture anchors of such embodiments may still be considered unitary as described herein. The outer surface 120 of the suture anchor 100 illustrated in FIGS. 1, 2, 4, 5, and 7 includes threads to engage with the bone 5. In other embodiments, the outer surface may include teeth or other protrusions for engaging with a bone. Some such teeth or other protrusions may facilitate a push-in insertion where rotation of the suture anchor to achieve implantation is not advantageous. Threads, teeth, or other protrusions of various embodiments may be raked to particularly prevent pull-out of a suture anchor or may be rectangular or symmetrical in a proximal-distal dimension to resist movement of a suture anchor once implanted in a bone.

Figure 1:
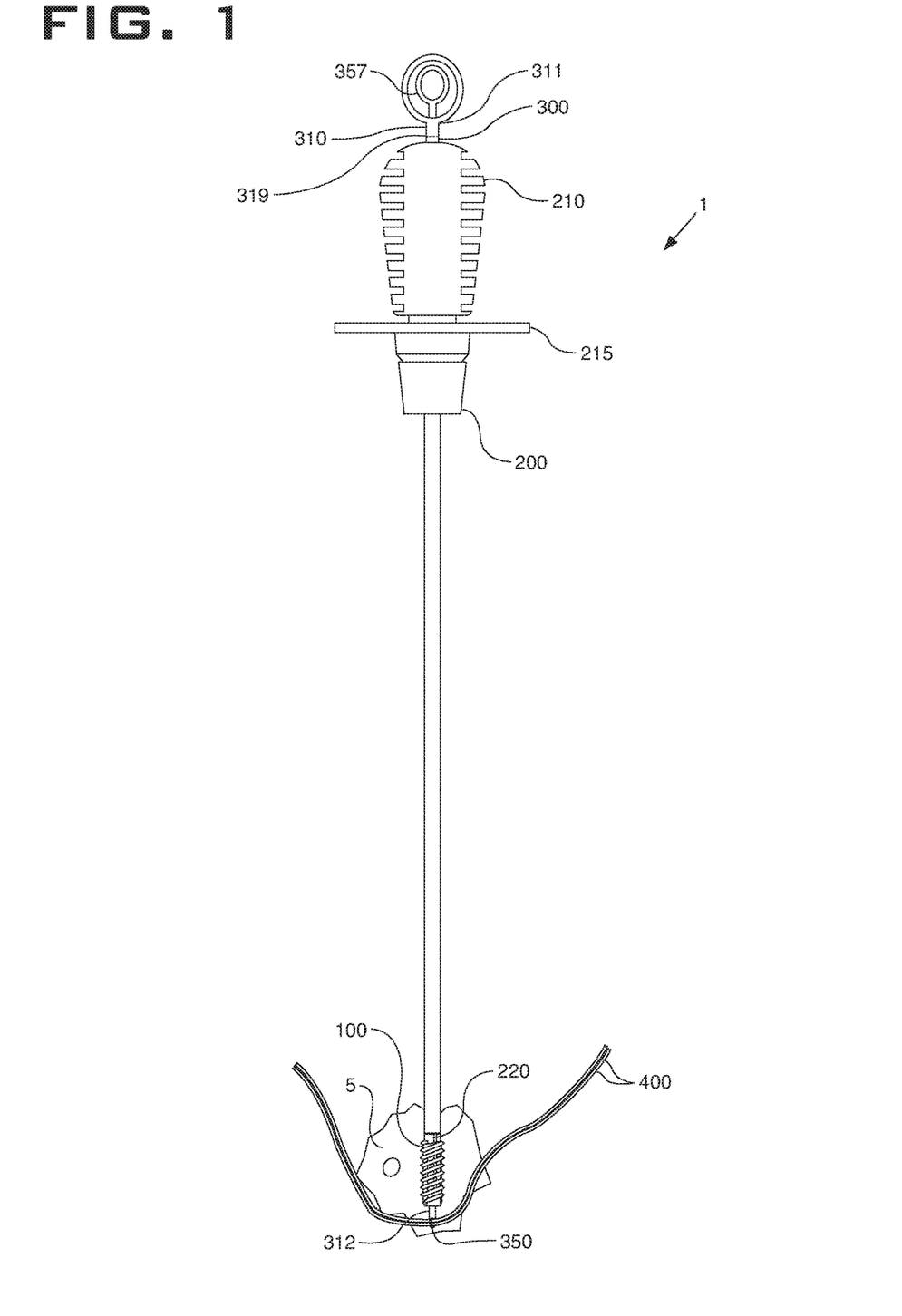
FIG. 1 is a side elevation view of an embodiment of a suturing system in a first state of operation.
Figure 2:
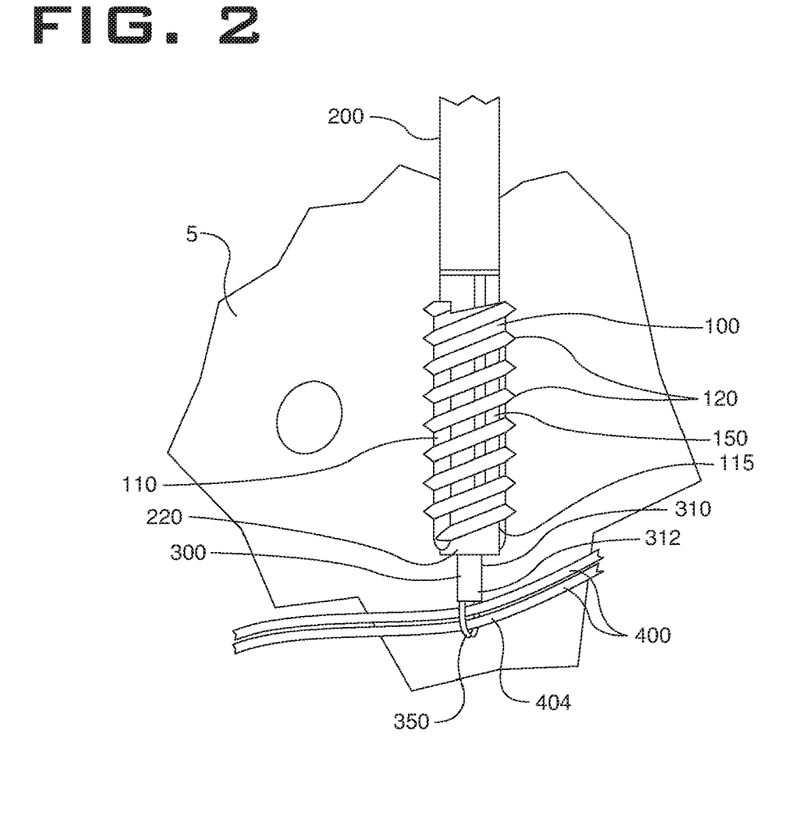
FIG. 2 is an enlarged side elevation view of a distal end of the embodiment of the suturing system illustrated in FIG. 1.
Figure 4:
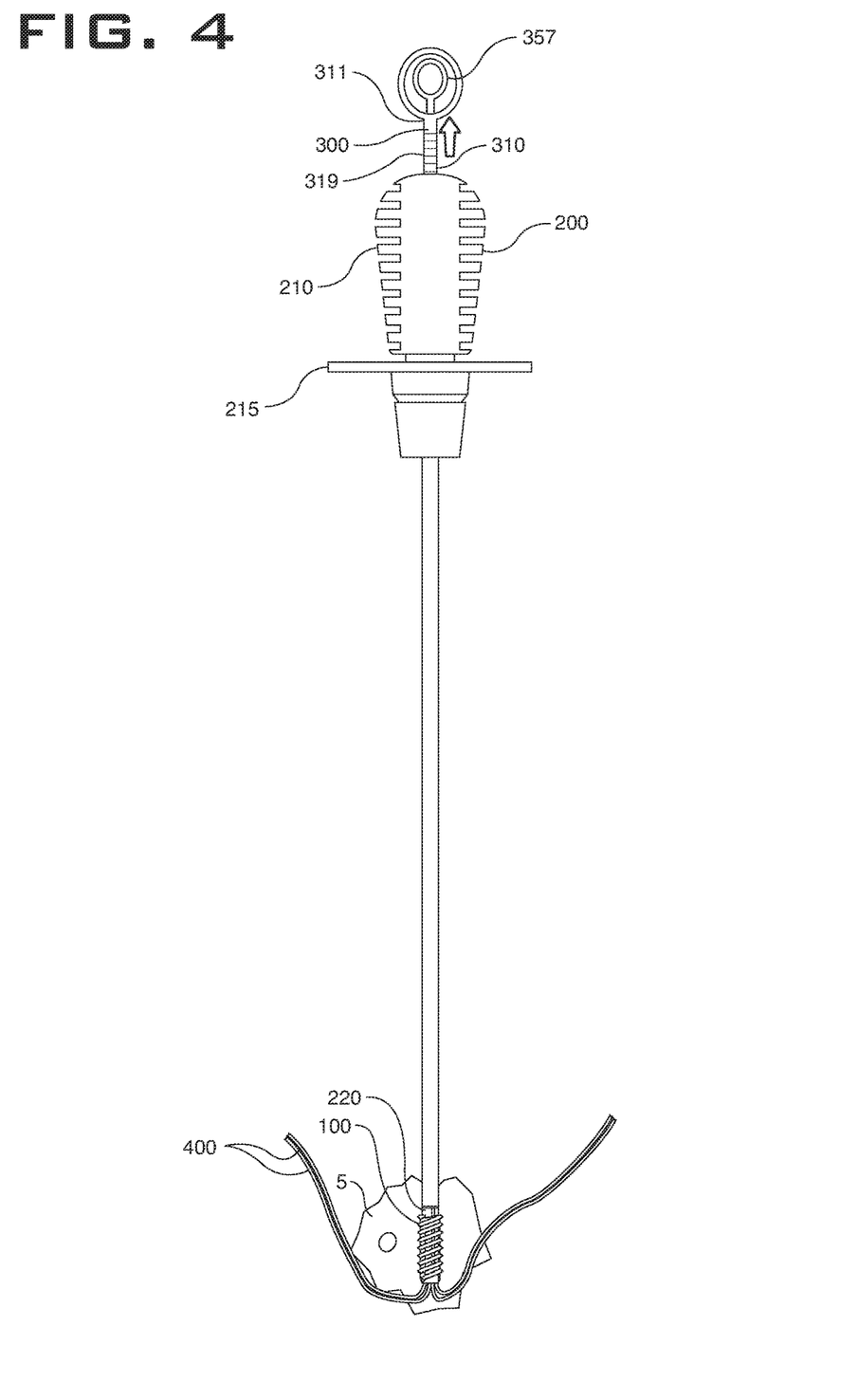
FIG. 4 is a side elevation view of the suturing system in a second state of operation.
Figure 5:
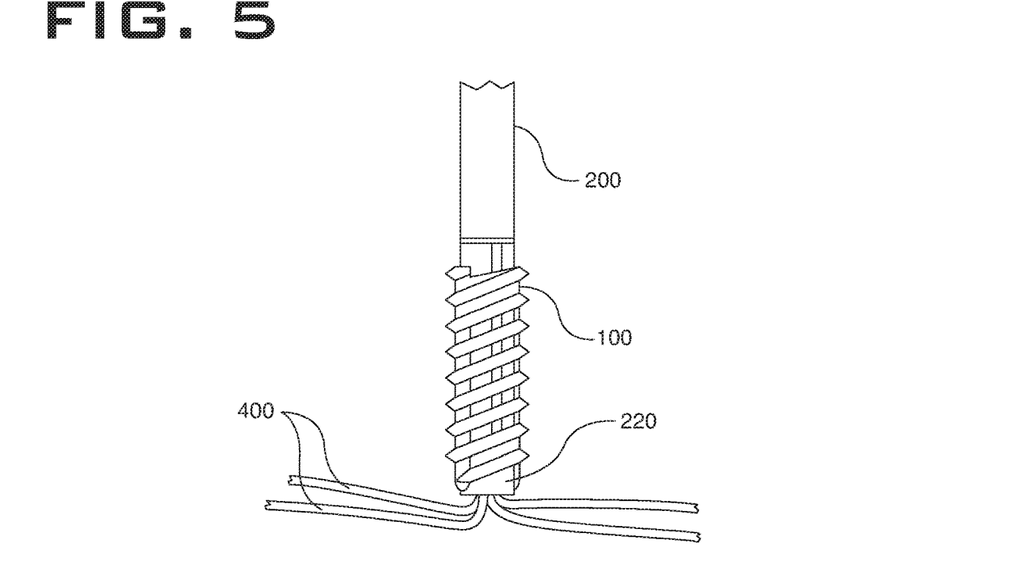
FIG. 5 is an enlarged side elevation view of a distal end of the embodiment of the suturing system as illustrated in FIG. 4.

The embodiment of the inserter 200 shown collectively in FIGS. 1, 2, 4, and 5 has a proximal end 210 configured to be manipulated by a user, and a distal end 220 configured to releasably engage with the suture anchor 100. An actuator 215 is also shown in FIGS. 1 and 4 that may be moved to lock and release the inserter 200 relative to the suture anchor 100. In other embodiments, any other effective mechanism may be used to create a releasable coupling between a suture anchor and an inserter. For example and without limitation, releasable coupling may be achieved by expanding of a distal end of the inserter in the suture anchor, by locking of a part of the distal end of the inserter with the suture anchor, or by attachment of a stay suture between an inserter and a suture anchor.

Embodiments of the suture puller 300 are configured to be proximally and distally movable relative to the inserter 200. The suture puller 300 illustrated in FIGS. 1-4, 6A, and 6B includes a shaft 310 with a proximal end 311 and a distal end 312. The suture puller 300 depicted also includes a suture retainer 350 near the distal end 312 of the shaft 310. The suture retainer 350 depicted in this embodiment is configured and sized to fit into the cannulation 115 (FIGS. 2 and 7) through the body 110 of the suture anchor 100 (FIGS. 4 and 5) to couple to a portion of a suture 400 near a distal end of the suture anchor 100 and be used to pull the portion of the suture 400 proximally into the suture anchor 100. In the illustrated example of FIGS. 4 and 5, the suture retainer 350 is also configured and sized to fit into a cannulation through the longitudinal length of the inserter 200, where the inserter 200, in turn, fits through the suture anchor 100. The suture puller 300 shown includes indicia 319 (FIGS. 1, 4, and 6B) near the proximal end of the suture puller 300 configured to measure a relative proximal-distal movement between the suture puller 300 and the inserter 200. For example, as shown in FIGS. 1 and 4, fewer indicia 319 are visible in FIG. 1, where the suture retainer 350 is extending from suture anchor 100, than in FIG. 4, where the suture puller 300 has been moved proximally relative to the suture anchor 100 that is coupled to the inserter 200. By observing the difference between the position in FIG. 1 and the position in FIG. 4, a user is able to determine how far the suture 400 has been drawn into the suture puller 300.

Figure 3:
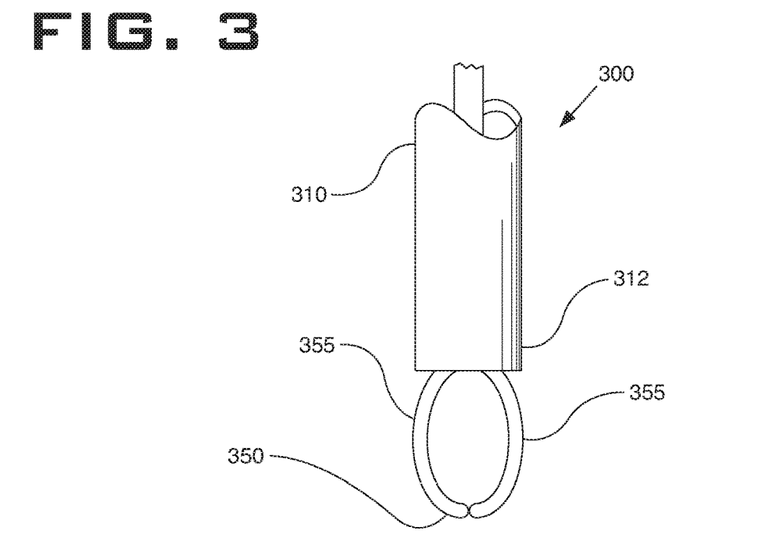
FIG. 3 is a side elevation view of a distal end of a suture puller of the suturing system illustrated in FIG. 2.
Figure 6A:
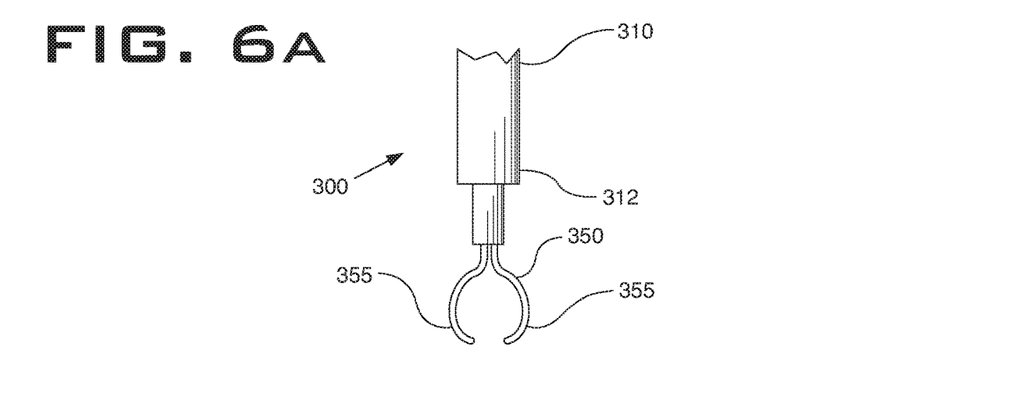
FIG. 6A is a side elevation view of an enlarged distal end of the suture puller of the suturing system with the suturing system in a third state.

As most clearly illustrated in FIGS. 3 and 6A, the suture retainer 350 shown is a selectively releasable mechanism that may be closed (FIG. 3) or opened (FIG. 6A) to, respectively, capture or release a suture 400 within the suture retainer 350. The suture retainer 350 depicted includes opposing non-returned (partial) hook arms 355 that cooperated to form an eyelet in which the suture 400 may be coupled. In other embodiments, a suture retainer may include returned hook arms. By "returned" it is meant that an end of the hook of a hook arm may point at least in part toward the proximal end 311 of the shaft 310. In some embodiments, a returned or non-returned hook of one arm may interact with a straight cooperating arm or member of some other effective configuration, or some embodiments may include only a single suture capturing arm. In some embodiments, a suture retainer may be a grasping or pinching mechanism rather than a hook or eyelet. In some embodiments, a suture retainer may be an eyelet that does not open and close, but instead through which the suture 400 may be feed and pulled proximally, where the suture 400 may be cut to be released from the eyelet in some method applications.

Figure 6B:
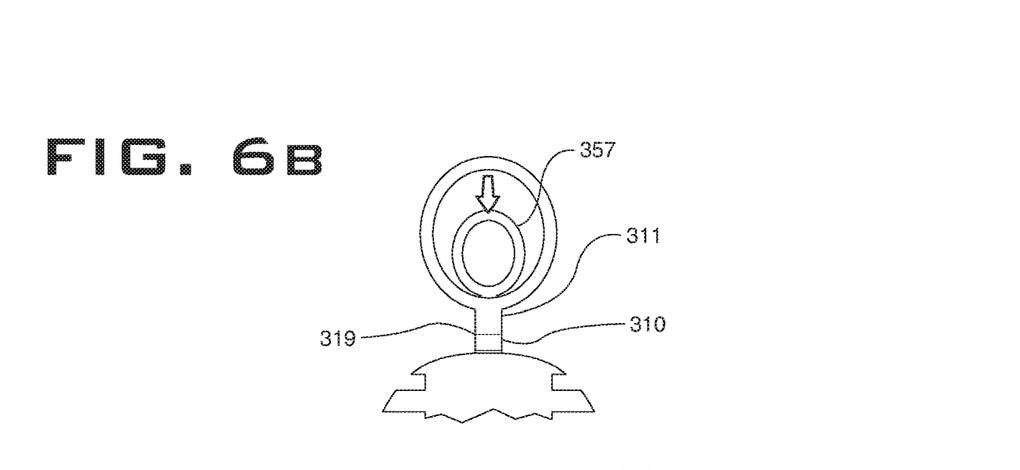
FIG. 6B is a side elevation view of an unenlarged proximal end of the suture puller in the third state shown in FIG. 6A.
Figure 7:
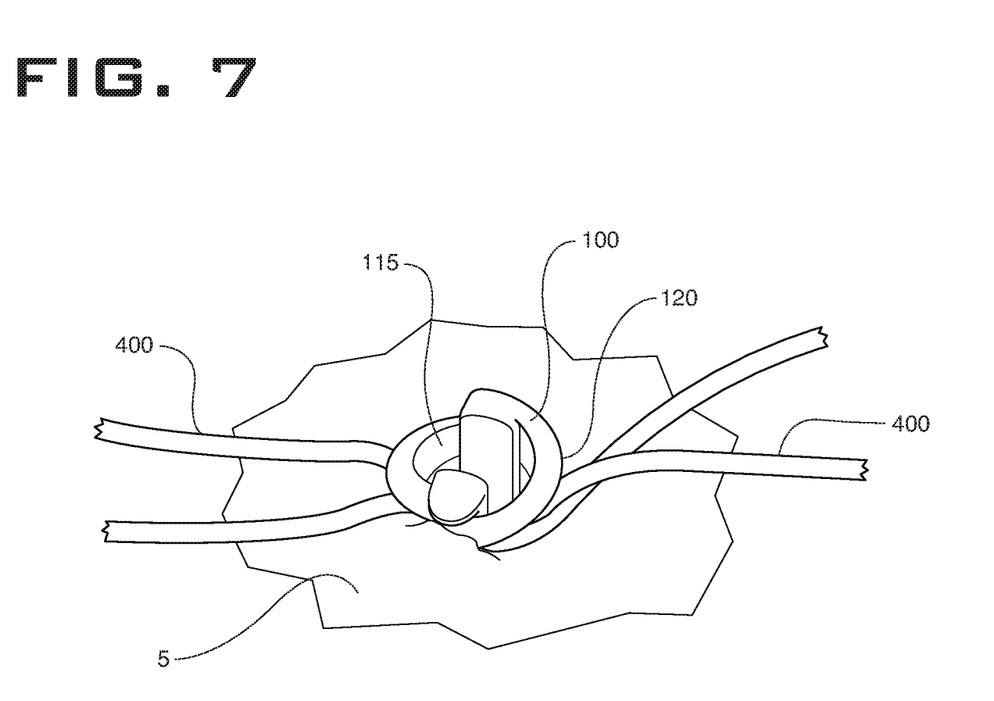
FIG. 7 is a perspective view of a suture anchor and suture of the suturing system illustrated in FIG. 1 implanted in bone.

In the illustrated embodiment, the suture retainer 350 is movable relative to the shaft 310 to close and open the hook arms 355. In particular, the suture retainer 350 includes a proximal actuator 357 (FIGS. 1, 4, and 6B) that is coupled to the hook arms 355 and is movable along a proximal-distal axis relative to the proximal end 311 of the shaft 310. In operation, when the proximal actuator 357 is in a more proximal position relative to the proximal end 311 of the shaft 310, as shown in FIGS. 1 and 4, the hook arms 355 are moved together and are capable of coupling with the suture 400, as shown in FIGS. 1-3. When the proximal actuator 357 is in a more distal position relative to the proximal end 311 of the shaft 310, as shown in FIG. 6B, the hook arms 355 are moved apart and capable of releasing the suture 400 from the suture retainer 350, as shown in FIG. 6A. In the illustrated embodiment, the shape of the hook arms 355 and their interaction with the distal end 312 of the shaft 310 (FIG. 3) causes a closing reaction between the hook arms 355 when the suture retainer 350 is in a proximal position relative to the shaft 310. In other embodiments, any other effective closing mechanism may be employed.

The suture 400 may be any functional suture, for example and without limitation, the suture may be a monofilament, multistrand, or woven construct. In some embodiments, the suture anchor 100 may be used to attach a tissue graft to another tissue element. For example and without limitation, the suture anchor 100 may be used to attach a ligament graft to a bone. A ligament graft or multiple grafts may be coupled to the suture anchor and screwed or pushed into a bone in an essentially similar manner to the illustrated suture 400. In various embodiments, one or any number of sutures may be coupled to a suture anchor to achieve surgical objectives, as limited only by the sizes of the sutures relative to the other functional components.

Suturing system embodiments may further include one or more additional suture anchors, such as but not limited to one or more of the suture anchors 100. Such system embodiments may be configured to capture the same suture 400 or one or more additional sutures extending from the first suture anchor 100 of the suturing system or extending from other sources. The one or more additional sutures may also be sized to fit within the suture retainer 350.

A suturing system 1001 with a suture anchor 1100, an inserter 1200, a suture puller 1300, a tube 1500, and a suture 400 are shown in whole and in respective part in FIGS. 8-13.

Figure 8:
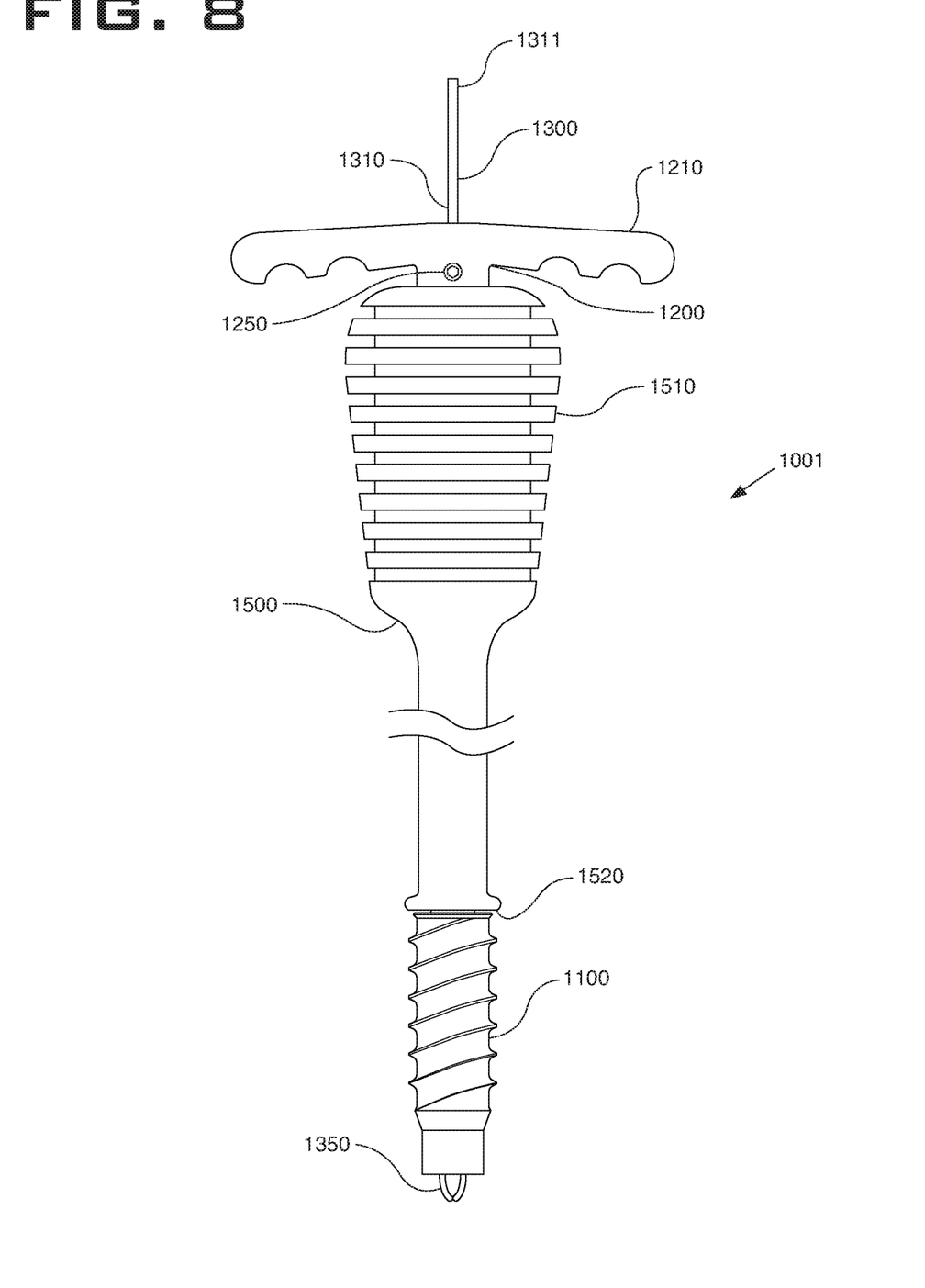
FIG. 8 is a side elevation view of an embodiment of a suturing system in a first state of operation.
Figure 9:
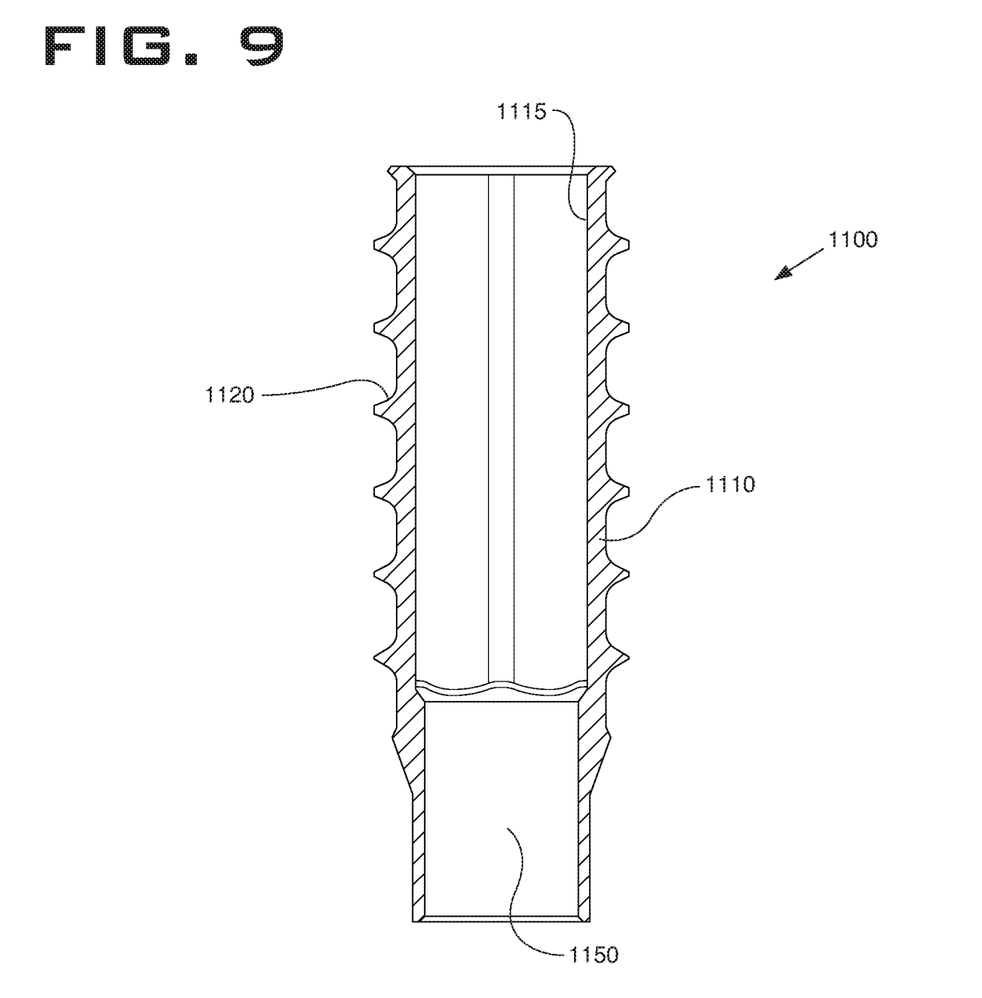
FIG. 9 is a side cross-sectional view of a suture anchor of the suturing system illustrated in FIG. 8.

The suture anchor 1100, as shown in more detail in FIG. 9, may include a body 1110 that has an outer surface 1120 configured to engage with a bone 55 (FIGS. 11-13) in which the suture anchor 1100 is implantable, and a cannulation 1115 through the body 1110. The suture anchor 1100 includes an open distal end through which the suture puller 1300 may be used. The illustrated suture anchor 1100 is a unitary suture anchor having no components that are adjustable relative to one another. It is known in the prior art to manage suture tension by providing suture anchors that have parts that move relative to one another and clamp or pinch suture between the part upon activation. This, however, requires greater manufacturing expense and complexity. Some embodiments may include more than one part, but where the multiple parts do not affect a unitary type effective function of the device, the suture anchors of the embodiments may still be considered unitary as described herein. The outer surface 1120 of the suture anchor 1100 illustrated in FIGS. 8-13 includes threads to engage with the bone 55. In other embodiments, the outer surface may include teeth or other protrusions for engaging with a bone. Some such teeth or other protrusions may facilitate a push-in insertion where rotation of the suture anchor to achieve implantation is not advantageous. Threads, teeth, or other protrusions of various embodiments may be raked to particularly prevent pull-out of a suture anchor or may be rectangular or symmetrical in a proximal-distal dimension to resist movement of a suture anchor once implanted in a bone.

The embodiment of the inserter 1200 shown collectively in FIGS. 8 and 10-13 has a proximal end 1210 configured to be manipulated by a user, and a distal end 1220 configured to releasably engage with the suture anchor 1100. The illustrated distal end 1220 has a hexagonal outer surface to engage with the cannulation 1115. Any other effective shape or style of distal end and cannulation may be used in other embodiments. For example and without limitation, the distal end and cannulation may be shaped as a slot, square, or star interface.

Embodiments of the inserter 1200 may include an actuator that may be moved to lock and release the inserter 1200 relative to the suture anchor 1100. In other embodiments, any other effective mechanism may be used to create a releasable coupling between a suture anchor and an inserter. For example and without limitation, releasable coupling may be achieved by expanding of a distal end of the inserter in the suture anchor, by locking of a part of the distal end of the inserter with the suture anchor, or by attachment of a stay suture between an inserter and a suture anchor.

Embodiments of the suture puller 1300 are configured to be proximally and distally movable relative to the inserter 1200. The inserter 1200 illustrated includes a locking screw 1250 that may be tightened or loosened to create a coupling or release between the inserter 1200 and the suture puller 1300. The suture puller 1300 illustrated in FIGS. 8 and 10-13 includes a shaft 1310 with a proximal end 1311 and a distal end 1312. The suture puller 1300 depicted also includes a suture retainer 1350 near the distal end 1312 of the shaft 1310. The suture retainer 1350 depicted in this embodiment is configured and sized to fit into the cannulation 1115 through the body 1110 of the suture anchor 1100 (FIGS. 10-13) to couple to a portion of a suture 400 near a distal end of the suture anchor 1100 and be used to pull the portion of the suture 400 proximally into the suture anchor 1100. In the illustrated example of FIGS. 8 and 10-13, the suture retainer 1350 is also configured and sized to fit into a cannulation through the longitudinal length of the inserter 1200, where the inserter 1200, in turn, fits through the suture anchor 1100.

Figure 13:
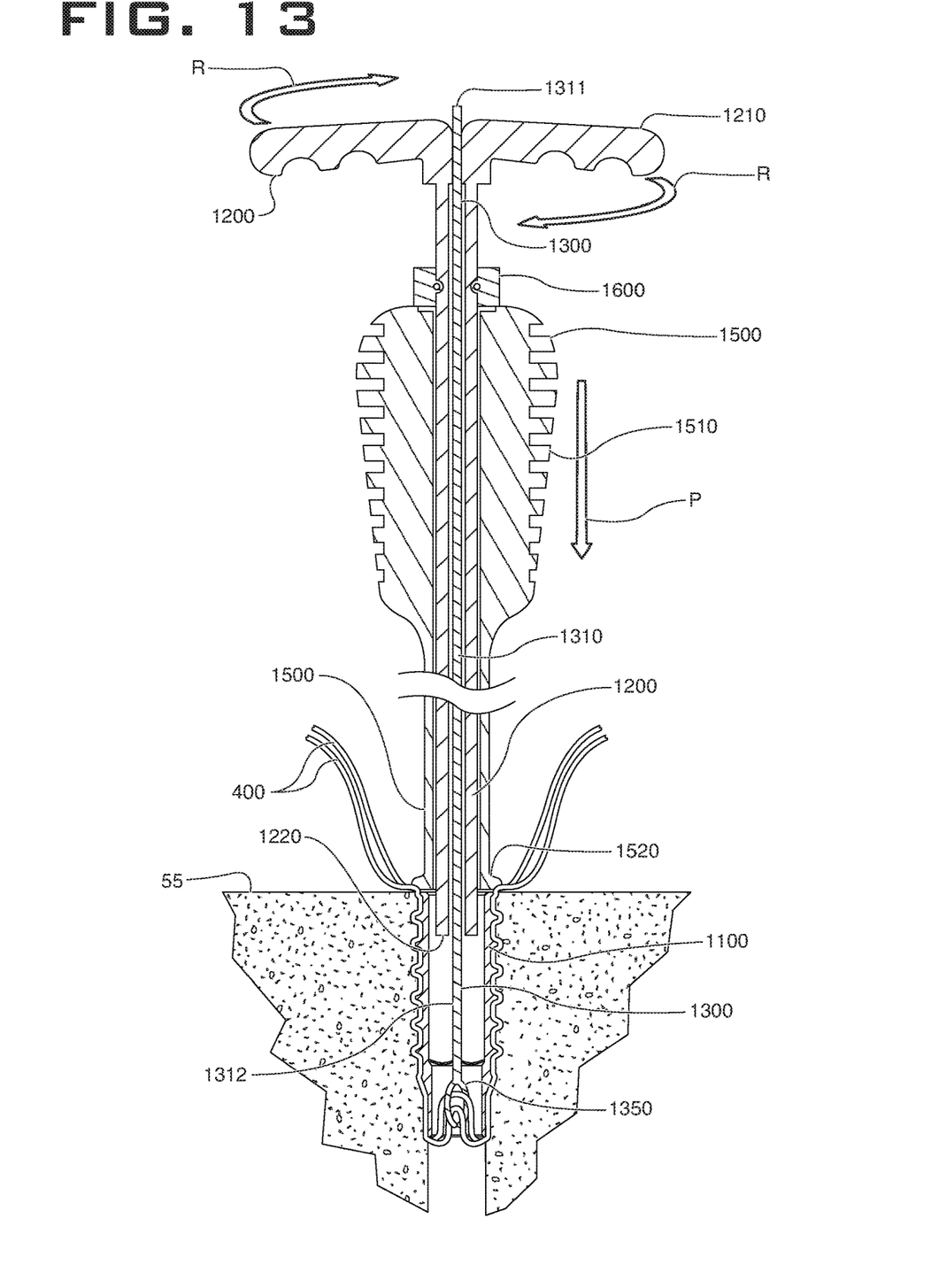
FIG. 13 is a side cross-sectional view of the suturing system illustrated in FIG. 8 in a fourth state of operation.

In the illustrated embodiment, the tube 1500 includes a handle 1510 near its proximal end and a stop 1520 near its distal end. The handle 1510 may be used to guide and apply distally or proximally directed forces to the tube 1500 and other components of the suturing system 1001. The stop 1520 may provide an indication to a user when the suture anchor 1100 coupled to the inserter 1200 has been implanted to be flush with a surface of the bone 55, as illustrated in FIG. 13, or has otherwise been advanced to a selectively predetermined depth in the bone. The suture retainer 1350 may be a selectively releasable mechanism or may be an eyelet, as is described in detail in association with the suture retainer 350 disclosed herein. The suture 400 may be any functional suture, as is described in detail herein.

Figure 10:
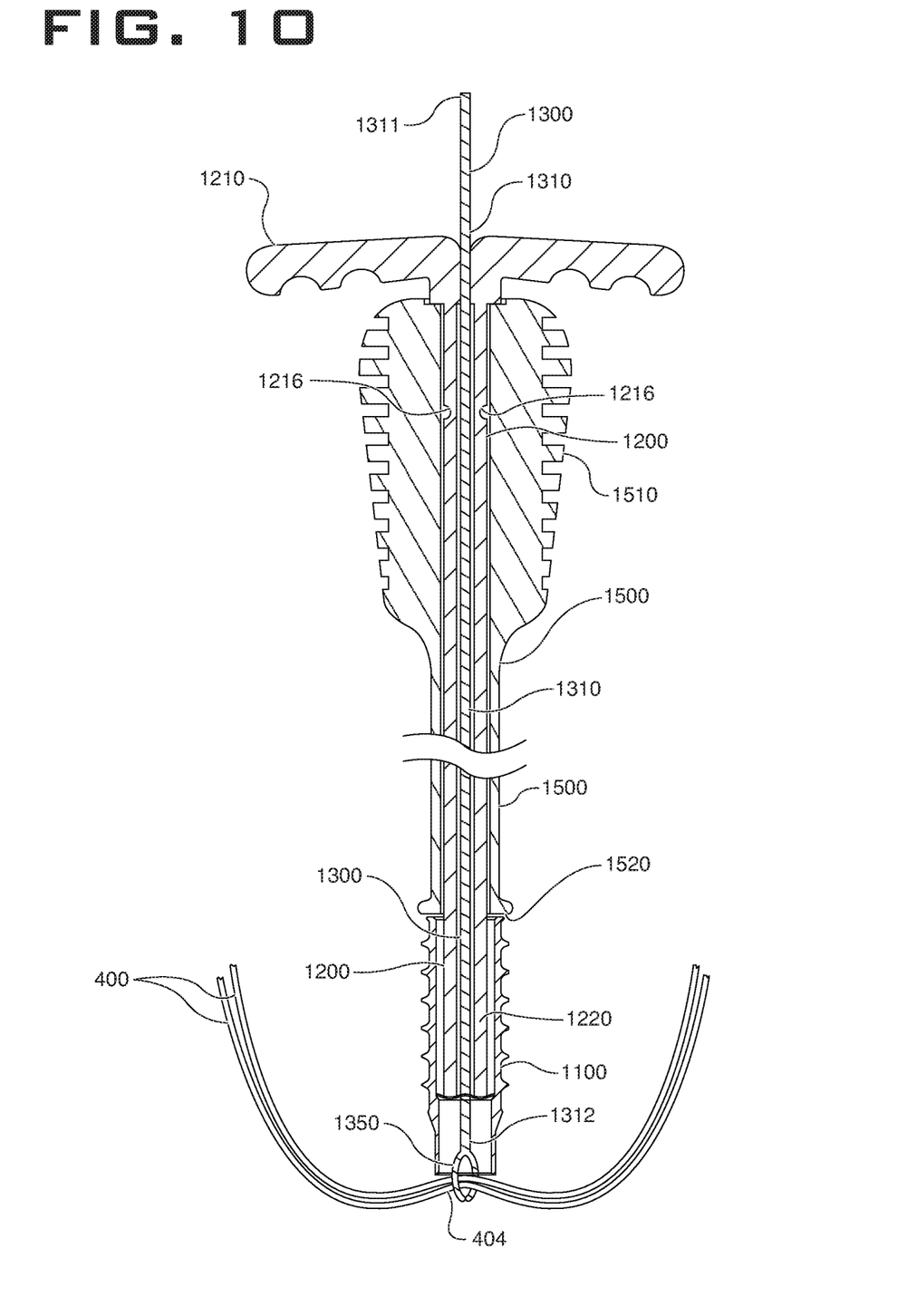
FIG. 10 is a side cross-sectional view of the suturing system illustrated in FIG. 8 in a first state of operation.

The suturing system 1001 also includes a lock 1600 (FIGS. 11-13) that may be coupled to the inserter 1200 to prevent movement along a proximal-distal axis between the inserter 1200 and the tube 1500. As shown in FIG. 10, one or more indents 1216 are provided on the inserter 1200 in which portions of the lock 1600 may be inserted to prevent the inserter 1200 from moving distally relative to the tube 1500.

Suturing system embodiments may further include one or more additional suture anchors, such as but not limited to one or more of the suture anchors 1100. Such system embodiments may be configured to capture the same suture 400 or one or more additional sutures extending from the first suture anchor 1100 of the suturing system or extending from other sources. The one or more additional sutures may also be sized to fit within the suture retainer 1350.

A general description for the use of the suturing system includes using one or more of the suture anchors 100, 1100 to accomplish a surgical or educational procedure. A method embodiment of the invention includes concurrently implanting a suture 400 and a suture anchor 100, 1100 into a bone 5, 55. Embodiments of the method may include drawing a length 404 (FIGS. 2 and 11) of suture 400 into a cavity 150 (FIG. 2), 1150 (FIG. 9) in the suture anchor 100, 1100. In particular in the embodiments illustrated, drawing the length 404 of suture 400 into the cavity 150, 1150 includes coupling the length 404 of suture 400 with a suture puller 300, 1300 and moving the suture puller proximally away from the bone 5, 55. In some embodiments, drawing the length 404 of suture 400 into a cavity 150 in the suture anchor 100 includes observing indicia 319 on the suture puller 300 to measure how far the length 404 of suture 400 is drawn into the suture anchor 100 by comparing relative positioning of the indicia 319 compared with the inserter 200 that is in a fixed position relative to the suture anchor 100.

Figure 11:
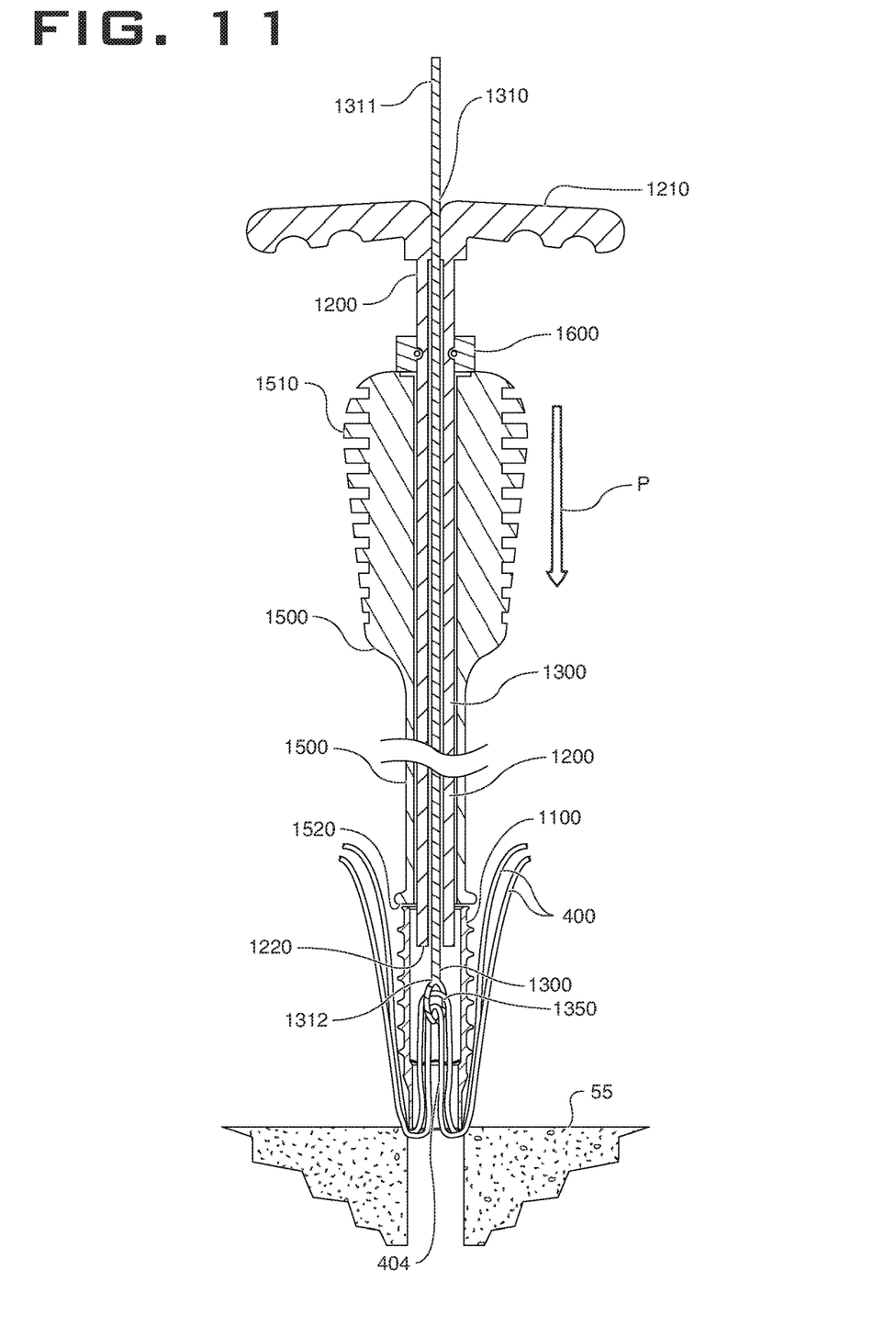
FIG. 11 is a side cross-sectional view of the suturing system illustrated in FIG. 8 in a second state of operation.
Figure 12:
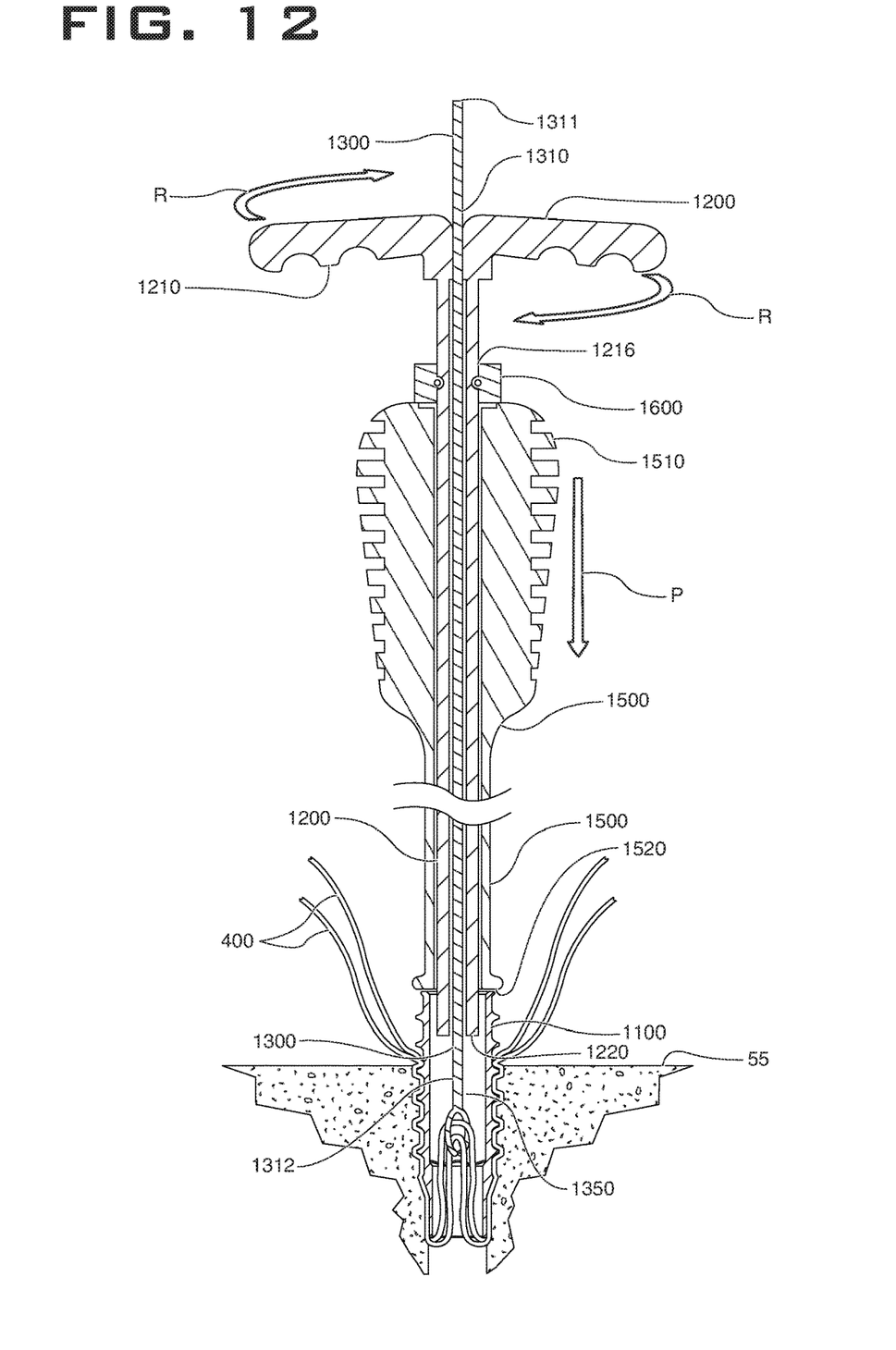
FIG. 12 is a side cross-sectional view of the suturing system illustrated in FIG. 8 in a third state of operation.

Some embodiments may also include moving the suture anchor 100, 1100 distally into the bone 5, 55 to implant the suture anchor 100, 1100 into the bone 5, 55 while allowing the length 404 of suture 400 drawn into the suture anchor 100, 1100 to be drawn out of the suture anchor 100, 1100 distally proportional to the amount the suture anchor 100, 1100 is moved distally into the bone 5, 55. As used herein, drawing out of the suture 400 distally proportional to the amount the suture anchor 100, 1100 is moved distally means the drawing out occurs with distal movement into the bone 5, 55, but does not necessarily mean that the amount drawn out is precisely the same distance as the amount moved distally. In various embodiments, the act of moving the suture anchor 100, 1100 distally may include one or both of pushing the suture anchor 100, 1100 distally and rotating the suture anchor 100, 1100. For example, the action arrow "P" in FIGS. 11-13 indicates pushing distally by pushing on the handle 1510 of the tube 1500. Rotation of the suture anchor 1100 is indicated by the action arrows "R" applied to the inserter 1200, which is coupled to the suture anchor 1100, as shown in FIGS. 12 and 13. Similar pushing and rotation may be applied to the inserter 200 for the embodiment of the suture anchor 100 shown in FIGS. 1, 2, 4, and 5.

Allowing the length 404 of suture 400 drawn into the suture anchor 100, 1100 to be drawn out of the suture anchor 100, 1100 distally proportional to the amount the suture anchor 100, 1100 is moved distally into the bone 5, 55 may include releasing the length 404 of suture 400 from the suture puller 300, 1300 used to draw the length 404 of suture 400 into the cavity 150, 1150 in the suture anchor 100, 1100. Release may be a result of opening the suture retainer 350, as shown in FIG. 6A, or could result from cutting of the suture in other embodiments. In some embodiments, such as the embodiment of FIGS. 11-13, the suture puller 1300 is moved distally as the suture anchor 1100 is moved distally before releasing the length of suture. In this example, distal movement of the suture puller may be enabled by loosening of the locking screw 1250 to allow the suture puller 1300 to move relative to the inserter 1200. In some embodiments, a spring force or other force or configuration may limit movement of the suture puller 300, 1300 relative to the inserter 200, 1200, even after loosening of a holding component such as the locking screw 1250. In some embodiments, such a spring force or other force is a consistent proximal tension. In some embodiments, the suture puller 300, 1300 is rotated with the suture anchor 100, 1100 as the suture anchor 100, 1100 is rotated and moved distally into the bone 5, 55.

In some embodiments, allowing the length 404 of suture 400 drawn into the suture anchor 100, 1100 to be drawn out of the suture anchor 100, 1100 distally proportional to the amount the suture anchor 100, 1100 is moved distally into the bone 5, 55 includes allowing the suture puller 300, 1300 used to draw the length 404 of suture 400 into the cavity 150, 1150 in the suture anchor 100, 1100 to be released and float freely relative to the inserter 200, 1200.

Referring to the example suturing system embodiment illustrated in FIGS. 8-13, a method embodiment of securing a suture to a bone is described immediately below. Acts of the method embodiment include placing an inserter 1200 within a tube 1500 and placing a suture anchor 1100 at a distal end of the tube 1500. The suture anchor 1100 shown is shown coupled with the inserter 1200 in FIGS. 8 and 10-13. The suture anchor 1100 is a unitary suture anchor, but in other embodiments may include multiple components, some of which may be moveable relative to one another. The method embodiment may also include placing a suture puller 1300 with a suture retainer 1350 near the distal end of the suture puller 1300 within the inserter 1200 and within the suture anchor 1100. Such placement is illustrated in FIGS. 8 and 10-13.

Method embodiments may also include moving the suture puller 1300 distally relative to the inserter 1200 and the suture anchor 1100 until the suture retainer 1350 is accessible from a distal end of the suture anchor 1100, as is shown in FIGS. 8 and 10; and coupling a length 404 (FIG. 10) of suture 400 with the suture retainer.

Additionally, methods may include moving the suture puller 1300 proximally relative to the suture anchor 1100 to draw the length 404 of suture 400 into a cavity 1150 in the suture anchor 1100. The act of drawing the length 404 of suture 400 into the cavity 1150 is illustrated by the progression between FIGS. 10 and 11. In this example, the locking screw 1250 (FIG. 8) is left secured to the inserter 1200 and the suture puller 1300 and the collective assembly is moved proximally to the position illustrated in FIG. 11. When in this position, the lock 1600 is put in place on the inserter by engaging the lock 1600 with the one or more indents 1216, as shown in FIG. 11. In some embodiments, indicia (not shown) may be included on the inserter 1200 such that moving the suture puller 1300 proximally relative to the suture anchor 1100 to draw the length 404 of suture 400 into the cavity 1150 in the suture anchor 1100 includes observing the indicia on the inserter 1200 to measure how far the length 404 of suture 400 is drawn into the suture anchor 1100 by comparing relative positioning of the indicia compared with the tube 1500 that is in a fixed position relative to the suture anchor 1100. In the embodiment illustrated, the distal end 1220 of the inserter 1200 moves proximally in the suture anchor 1100, but remains rotationally engaged so that rotation of the inserter 1200 results in rotation of the suture anchor 1100.

Method embodiments may also include moving the tube 1500 and the suture anchor 1100 distally into the bone 55 to implant the suture anchor 1100 into the bone 55 while allowing the length 404 of suture 400 drawn into the suture anchor 1100 to be drawn out of the suture anchor 1100 distally proportional to the amount the tube 1500 and the suture anchor 1100 are moved distally into the bone 55. This sequence of movement is illustrated in FIGS. 11-13. Specifically, a linear pushing force is represented by action arrows "P" and partial distal movement is shown in FIG. 12, with additional distal movement shown in FIG. 13. Because the suture anchor 1100 is a threaded device, distal movement shown is also encouraged by rotating the suture anchor 1100 about its longitudinal axis by rotating the inserter 1200, as indicated by action arrows "R" in FIGS. 12 and 13. In other embodiments, especially where a suture anchor is intended to be inserted solely by a pushing force, the suture anchor may not be rotated during distal movement. Similarly, where an anchor includes a sufficiently aggressive thread pattern, rotation may be sufficient to move the suture implant distally, without the necessity for distal, linear pushing.

As may be observed in the progression from FIGS. 11-13, in this embodiment, the suture puller 1300 is released relative to the inserter 1200 (by loosening of the locking screw 1250 shown in FIG. 8) and the length 404 of suture 400 drawn into the suture anchor 1100 is drawn out of the suture anchor 1100 distally proportional to the amount the tube 1500 and the suture anchor 1100 are moved distally into the bone 55. In other words, in the illustrated embodiment the length 404 of suture 400 drawn into the suture anchor 1100 is allowed to be drawn out of the suture anchor 1100 distally proportional to the amount the tube 1500 and the suture anchor 1100 are moved distally into the bone 55 by holding the length 404 of suture 400 in the suture retainer 1350 of the suture puller 1300 used to draw the length 404 of suture 400 into the cavity 1150 in the suture anchor 1100 and moving the suture puller 1300 distally as the tube 1500 and the suture anchor 1100 are moved distally. Specifically, in the embodiment depicted, the suture puller 1300 is released relative to the inserter 1200 and allowed to float freely relative to the tube 1500 and the inserter 1200. In other embodiments, a suture puller may be specifically rotated with the suture anchor as the tube and the suture anchor are rotated and moved distally into the bone. This may result in less length 404 of the suture being drawn out distally as the suture anchor is moved distally. In still other embodiments, a consistent proximal tension may be applied on a suture puller relative to the inserter, such as a spring force, while the suture anchor is moved distally.

In some embodiments, the length 404 of suture 400 drawn into suture anchor 1100 may be drawn out of the suture anchor 1100 distally proportional to the amount the tube 1500 and the suture anchor 11000 are moved distally into the bone 55 by releasing the length 404 of suture 400 from the suture puller 1300. Such a release may be the result of cutting the suture 400, for example along the length 404, or may include opening or unclamping suture 400 from a suture retainer of such embodiments.

Method embodiments may include but are not limited to securing a suture to bone in performing a rotator cuff repair consistent with the acts described herein. In particular, the anchor system 1, 1001 may be used to secure a suture, such as the suture 400 to a humerus where one or more sutures 400 have been attached to soft tissues of the rotator cuff. In the particular example of a double-row rotator cuff repair, a suture anchor 100, 1100 of the anchor system 1, 1001 may be used to secure one or more sutures 400 to a humerus underneath soft tissues of the rotator cuff. The suture anchor 100, 1100 may also be used to secure one or more sutures 400 into a humerus distal of the soft tissues of the rotator cuff. A common suture may be passed between and coupled to two or more suture anchors 100, 1100 of such a construct or multiple sutures may be combined by tying or by coupling to two or more suture anchors 100, 1100.

Other method embodiments may include use of devices disclosed herein to perform a labral repair. For example and without limitation, one or more suture anchors 100, 1100 may be inserted into a glenoid bone. One or more sutures 400 attached to the suture anchors 100, 1100 may then be used to re-attach the labrum to the bone. A typical labral repair may require 1, 2, 3, or more suture anchors 100, 1100, depending on the location and size of the tear being repaired. After the one or more suture anchors 100, 1100 are placed, sutures 400 may be run through the labrum and then pulled tight to re-attach the labrum to the glenoid. A common suture 400 may be passed between and coupled to two or more suture anchors, 100, 1100 of such a construct or multiple sutures 400 may be combined by tying or by coupling to two or more suture anchors 100, 1100.

Various embodiments of a system wholly or its components individually may be made from any biocompatible material. Instruments that will not be implanted and remain in a patient may not necessarily be biocompatible. For example and without limitation, materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol, and other superelastic or shape-memory metal alloys. Sutures or other similar components of the invention may be single strand, woven, braided, or any combination thereof from any of these or other biocompatible materials. The sutures or other similar components may be any effective natural or synthetic material and may be a use or combination of materials well-known in the art. Sutures or other similar components of various embodiments may be resorbable or not resorbable.

Terms such as proximal, distal, far, underneath, enlarged, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A method of concurrently implanting a suture and a suture anchor into a bone comprising:
    drawing a length of suture into a cavity in the suture anchor with a suture puller; and
    holding the length of suture within the suture anchor with the suture puller; and while holding;
    moving the suture anchor distally into the bone to implant the suture anchor into the bone while allowing the length of suture drawn into the suture anchor to be drawn out of the suture anchor distally proportional to the amount the suture anchor is moved distally into the bone.

2. The method of claim 1 wherein concurrently implanting a suture and a suture anchor includes implanting a unitary suture anchor.

3. The method of claim 1 wherein the act of drawing a length of suture into a cavity in the suture anchor includes coupling to the length of suture with a suture puller and moving the suture puller proximally away from the bone.

4. The method of claim 3 wherein the act of drawing a length of suture into a cavity in the suture anchor includes observing indicia on the suture puller to measure how far the length of suture is drawn into the suture anchor by comparing relative positioning of the indicia compared with the inserter that is in a fixed position relative to the suture anchor.

5. The method of claim 1 wherein the act of moving the suture anchor distally into the bone includes pushing the suture anchor distally linearly.

6. The method of claim 1 wherein the act of moving the suture anchor distally into the bone includes rotating the suture anchor about its longitudinal axis.

7. The method of claim 1 wherein the act of moving the suture anchor distally into the bone includes pushing the suture anchor distally linearly and rotating the suture anchor about its longitudinal axis.

8. The method of claim 1 further comprising releasing the length of suture from a suture puller after moving the suture anchor distally into the bone.

9. The method of claim 1 further comprising moving the suture puller distally as the suture anchor is moved distally, then releasing the length of suture.

10. The method of claim 1 wherein allowing the length of suture drawn into the suture anchor to be drawn out of the suture anchor distally proportional to the amount the suture anchor is moved distally into the bone includes rotating a suture puller used to draw the length of suture into the cavity in the suture anchor with the suture anchor as the suture anchor is rotated and moved distally into the bone, then releasing the length of suture.

11. The method of claim 1 wherein allowing the length of suture drawn into the suture anchor to be drawn out of the suture anchor distally proportional to the amount the suture anchor is moved distally into the bone includes applying a consistent proximal tension on a suture puller used to draw the length of suture into the cavity in the suture anchor relative to the inserter while the suture anchor is implanted.

12. The method of claim 11 wherein applying a consistent proximal tension to the suture puller includes applying a spring mechanism between the suture puller and the inserter.

13. The method of claim 1 wherein allowing the length of suture drawn into the suture anchor to be drawn out of the suture anchor distally proportional to the amount the suture anchor is moved distally into the bone includes allowing a suture puller to be released and float freely relative to the inserter.

14. A method of securing a suture to a bone comprising:
placing an inserter within a tube;
placing a suture anchor at a distal end of the tube, wherein the suture anchor is configured to couple with the inserter;
placing a suture puller with a suture retainer near its distal end within the inserter and within the suture anchor;
positioning the suture puller distally relative to the inserter and the suture anchor so that the suture retainer is accessible from a distal end of the suture anchor;
coupling a length of suture with the suture retainer;
moving the suture puller proximally relative to the suture anchor to draw the length of suture into a cavity in the suture anchor; and while holding the length of suture within the suture anchor with the suture retainer;
moving the tube the suture anchor and the suture puller distally to implant the suture anchor into the bone while allowing the length of suture drawn into the suture anchor to be drawn out of the suture anchor distally proportional to the amount the suture anchor is moved distally into the bone; and
releasing the suture from the suture retainer.

15. The method of claim 14 wherein the suture anchor is a unitary suture anchor.

16. The method of claim 14 wherein the act of moving the suture puller proximally relative to the suture anchor to draw the length of suture into the cavity in the suture anchor includes observing indicia on the inserter to measure how far the length of suture is drawn into the suture anchor by comparing relative positioning of the indicia compared with the tube that is in a fixed position relative to the suture anchor.

17. The method of claim 14 wherein the act of moving the suture anchor distally includes pushing the suture anchor distally linearly.

18. The method of claim 14 wherein the act of moving the suture anchor includes rotating the suture anchor about its longitudinal axis.

19. The method of claim 14 wherein the act of moving the suture anchor distally includes pushing the suture anchor distally linearly and rotating the suture anchor about its longitudinal axis.

20. The method of claim 14 wherein allowing the length of suture drawn into the suture anchor to be drawn out of the suture anchor distally proportional to the amount the tube and the suture anchor are moved distally includes rotating the suture puller with the suture anchor.

21. The method of claim 14 wherein allowing the length of suture drawn into the suture anchor to be drawn out of the suture anchor distally proportional to the amount the tube and the suture anchor are moved distally includes applying a consistent proximal tension on the suture puller relative to the inserter or the tube while the suture anchor is implanted.

22. The method of claim 21 wherein applying a consistent proximal tension to the suture puller includes applying a spring mechanism between the suture puller and the inserter or the tube.

23. The method of claim 14 wherein allowing the length of suture drawn into the suture anchor to be drawn out of the suture anchor distally proportional to the amount the suture anchor is moved distally includes allowing the suture puller to be released and float freely relative to the tube and the inserter.

* * * * *